(12) United States Patent
Lillicrap et al.

(10) Patent No.: US 11,109,577 B2
(45) Date of Patent: Sep. 7, 2021

(54) DEVICE, METHOD, AND SYSTEM FOR DISTRIBUTING PESTICIDE IN A FISH PEN

(71) Applicant: NIVA, Oslo (NO)

(72) Inventors: Adam Lillicrap, Sofiemyr (NO);
Katherine Langford, Kolsås (NO);
Malcolm Reid, Oslo (NO)

(73) Assignee: NIVA, Oslo (NO)

(*) Notice: Subject to any disclaimer, the term of this patent is extended or adjusted under 35 U.S.C. 154(b) by 450 days.

(21) Appl. No.: 16/073,552

(22) PCT Filed: Jan. 27, 2017

(86) PCT No.: PCT/NO2017/050025
§ 371 (c)(1),
(2) Date: Jul. 27, 2018

(87) PCT Pub. No.: WO2017/142416
PCT Pub. Date: Aug. 24, 2017

(65) Prior Publication Data
US 2019/0075763 A1    Mar. 14, 2019

(30) Foreign Application Priority Data

Jan. 29, 2016    (NO) .................................... 20160137

(51) Int. Cl.
*A01K 61/13*    (2017.01)
*A61D 11/00*    (2006.01)
(Continued)

(52) U.S. Cl.
CPC .............. *A01K 61/13* (2017.01); *A01K 61/60* (2017.01); *A61D 11/00* (2013.01); *C02F 1/50* (2013.01);
(Continued)

(58) Field of Classification Search
CPC ................................ A01K 61/13; A01K 61/60
See application file for complete search history.

(56) References Cited

U.S. PATENT DOCUMENTS 4,228,614 A * 10/1980 Cardarelli .............. A01K 63/04
43/131
4,562,794 A    1/1986 Speckman
(Continued)

FOREIGN PATENT DOCUMENTS

AU    2014219519 A1    9/2015
WO    WO 91/01086 A1    2/1991
(Continued)

OTHER PUBLICATIONS

International Search Report and Written Opinion dated May 15, 2017 issued in International Application No. PCT/NO2017/050025.
(Continued)

*Primary Examiner* — Monica L Barlow
(74) *Attorney, Agent, or Firm* — Arent Fox, LLP (57) ABSTRACT

Device, system and method for distribution of pesticides to reduce or eliminate parasitic creatures liable to infest aquaculture facilities or the animals kept in these, such as salmon lice in a fish farm. The invention is based on the use of pesticides at a concentration level low enough to not represent a dangerous level for the environment, but for a longer exposure period, sufficient to enable delousing to occur.

18 Claims, 9 Drawing Sheets

(51) Int. Cl.
*C02F 1/50* (2006.01)
*C02F 1/68* (2006.01)
A01K 61/60 (2017.01)
*C02F 1/00* (2006.01)
*A01N 53/00* (2006.01)
*A61K 9/14* (2006.01)

(52) U.S. Cl.
CPC .............. *C02F 1/685* (2013.01); *A01N 53/00* (2013.01); *A61K 9/141* (2013.01); *C02F 1/008* (2013.01); *C02F 2209/02* (2013.01); *Y02A 40/81* (2018.01)

(56) References Cited

U.S. PATENT DOCUMENTS

| | | | | |
|---|---|---|---|---|
| 4,631,857 A | * | 12/1986 | Kase | ........................ A01M 1/20 43/131 |
| 4,880,547 A | * | 11/1989 | Etani | ........................ B05B 7/04 210/728 |
| 6,641,787 B1 | * | 11/2003 | Siggins | ................. B01F 1/0033 210/198.1 |
| 2003/0041505 A1 | | 3/2003 | Flinn et al. | |
| 2003/0140863 A1 | | 7/2003 | Aldrige et al. | |
| 2004/0185079 A1 | | 9/2004 | Zomer | |
| 2006/0188535 A1 | * | 8/2006 | Sjogren | ................. A01N 49/00 424/405 |
| 2006/0234867 A1 | * | 10/2006 | Dupree | ................. A01N 25/08 504/358 |

FOREIGN PATENT DOCUMENTS

| | | |
|---|---|---|
| WO | WO 03/077651 A1 | 9/2003 |
| WO | WO 2014/129908 A1 | 8/2014 |
| WO | WO 2015/122758 A1 | 8/2015 |

OTHER PUBLICATIONS

Norwegian Search Report dated Aug. 24, 2016 issued in Norwegian Application No. No 20160137.

* cited by examiner

| Active ingredient | Country | Amount used in 2014 (tonnes) | Treatment and duration of treatment | Acute toxicity (µg/L) | Chronic toxicity (µg/L) |
|---|---|---|---|---|---|
| Azamethiphos | Norway | 4630 | Bath <1 hour | 7 | 4 |
| | Scotland | 253 | | | |
| Cypermethrin | Norway | 162 | Bath <1 hour | 0.0059 | 0.0015 |
| | Scotland | 0 | | | |
| Diflubenzuron | Norway | 5016 | In feed 7 days | >1000 | 0.010 |
| | Scotland | 0 | | | |
| Emamectin | Norway | 172 | Bath <1 hour | 1 | 0.088 |
| | Scotland | 64 | | | |
| Teflubenzuron | Norway | 2674 | In feed 7 days | >1000 | 0.0032 |
| | Scotland | 0 | | | |
| Hydrogen-peroxide 100% (tonne) | Norway | 31577 | Bath <1 hour | 2400 | 630 |

DEVICE, METHOD, AND SYSTEM FOR DISTRIBUTING PESTICIDE IN A FISH PEN

CROSS-REFERENCE TO RELATED APPLICATION

This application is a 35 U.S.C. § 371 National Phase of PCT Application No. PCT/NO2017/050025 filed Jan. 27, 2017, which claims priority to Norwegian Application No. NO20160137 filed Jan. 29, 2016. The disclosure of these prior applications are hereby incorporated by reference herein.

BACKGROUND

The invention relates to a system, method and device for treating aquaculture facilities (e.g. farmed fish).

Aquaculture is a globally important food production industry which has over the past years shown major growth. One example is the salmonid farming industry which represents a large portion of this industry in Europe and the Americas, being dominated by industry in Norway, Chile and Scotland.

A major problem for salmonid aquaculture is the infestation of salmon lice, and the use of pesticides is often vital to control these ectoparasites. Salmon lice infestations do not just have economic consequences due to the loss of sales, but it is also the problem of lice transmission from fish farms to wild salmonid stocks. In addition, to meet the increasing demand for salmon, the future expansion of fish farms is dependent on salmon lice levels being kept below 0.1 lice per fish. In 2014, the average salmon lice levels in Norwegian fish farms were just over 0.2 per fish (Ramsden, 2015) suggesting that current salmon lice control practices are not adequately controlling the situation.

The problem is further exacerbated by the rise of resistant strains to many of the products that are approved for use in aquaculture. In combination with the attempt to control salmon lice levels, is the possible environmental impact of the treatments where potential effects on non-target organisms may occur during and after treatment. This is partly due to aquaculture medicines often being toxic to non-target species in order to elicit the desired effect on sea lice. One such problem is caused by chitin synthesis inhibitors that are one group of chemicals that are typically not inherently acutely toxic to non-target organisms such as crustaceans but may cause long term developmental effects. Although the exact mode of action (MoA) of these substances is currently unknown, it is understood they affect reproduction and development of chitin synthesizing organisms, and typically induce malformations whilst reducing chitin production.

Current mechanisms for treating fish for salmon lice involve the use of pesticides. Methods for distributing pesticides are solved by either distributing the substances as an additive in the fodder, such that when the salmon eats and digest the food, the pesticides are transferred to the salmon lice attached to the fish, or by adding substantial levels of pesticides in a bath, so that when the salmon is kept in the bath for a period of time, long enough for the lice to die or detach, but short enough to not inflict too much stress to the salmon. Both methods have unwanted side effects, either to the environment or to the cost of operation.

The bath method comprises several drawbacks, for example moving the salmon to and from bath in a well boat or erecting tarpaulin around the fish pen to create a bath is a tedious and expensive processes involving a lot of manual overseeing and risks. It further exposes the fish to a lot of stress and discomfort, although a healthy fish will not die, it will certainly be affected for some time being exposed to the pesticides during the treatment period. Fish quality is linked to fish welfare.

The method of distributing pesticides in the fodder will possibly affect the environment in the vicinity of the fish farm, as the uneaten fodder will fall to the seafloor where it may be eaten by non target organisms or incorporated into the sediment. The feces of the fishes in the pen also contain a large concentration of non-absorbed pesticide, and this will either equilibrate in the water column or fall to the sea floor, where it will add to the level of pesticides already there.

SUMMARY

It is hence an objective for the present invention to provide a method, system and device for solving the above stated problems.

Although the scenarios below discusses treatment in fish pens, for example in salmon production, it should be understood that the system, methods and devices may be used for treating any type of aquaculture facilities comprising any type of live species. (e.g. farmed fish).

One aspect of the invention provides a method for distribution of pesticides to reduce or eliminate salmon lice in a fish farm. The invention is based on the use of pesticides at a concentration level low enough to not represent a dangerous level for the environment, but for a longer exposure period, sufficient to enable delousing to occur.

A second aspect of the invention is to provide a device for continuous distribution of pesticides. The device will release pesticides at a controlled rate for a prolonged period of time, typically days and weeks.

A third aspect of the invention is to provide a method and system for concurrently monitoring the pesticide concentration to enable a controlled supply of pesticides to the fish farm.

A fourth aspect of the invention is to provide a method and system for reduction of the actual amount of chemical that is needed for enabling a reduction or elimination of parasitic creatures in an aquaculture facility.

The following figures are provided as an aid to understand the concept of the invention, and shall not be regarded as limitations of the invention.

BRIEF DESCRIPTION OF THE DRAWINGS

FIG. 1B—Principle of hollow device
FIG. 1C'Cross section of FIG. 1A when hollow
FIG. 1D—Cross section of FIG. 1A when solid
FIG. 2—Distribution system in fish pen
FIG. 3—Table for lethal effect of concentration vs. length of treatment
FIG. 4—Sea lice lifecycle
FIG. 5—Fish pen—free floating distribution devices
FIG. 6—Fish pen—distribution devices in net
FIG. 7—System overview
FIG. 8—Flow chart
FIG. 9—Therapeutic dose graph mirroring present state
FIG. 10—Therapeutic dose graph equivalent dose for longer exposure duration
FIG. 11—Therapeutic dose graph significantly lower dose for longer exposure duration

DETAILED DESCRIPTION

Use of Word and Phrases:

When the phrase "Fish pen" is used it shall be understood that it shall also mean any type of aquaculture facilities wherein the device, method and system of the invention may be successfully implemented in order to reduce or terminate parasitic creatures.

When the phrase "Salmon lice" is used it shall be understood that it shall also mean any type of parasitic creatures liable to infest aquaculture facilities or the animals kept in these.

The invention is based on the idea that the effect of some pesticides may be distributed in very low concentrations directly into the water column inside the fish pen. The concentration may be so low that they do not represent any threats to any organisms in the waters outside the fish pen. If low concentrations are maintained inside the fish pen, the effect outside the fish pen is ignorable, based on the dilution rate once the water treated with pesticide is exposed to the surrounding water masses. The low concentration is however maintained over a long time, long enough for a salmon lice to concentrate the level of pesticide inside its body, until it will kill or prohibit growth in such a manner that they do not reach reproducing size/age.

Toxicity is a function of both the concentration and exposure duration. Hence, a pesticide at a low concentration can cause the same effect (e.g. death, developmental effects etc.) on salmon lice as a high concentration, if the exposure duration is long enough. The current treatment routine is to expose the salmon lice at high concentrations over a short duration. This results in pulses of highly concentrated pesticides being released. A slow, continuous exposure for a longer period of time will be (if not more) as effective on de-lousing the fish without having a negative impact on organisms in the surrounding vicinity.

In order to provide a slow release of pesticide, a pesticide release device is provided. The release device provides allocation of aquaculture medicines using a passive dosing approach with buoyant large surface-area delivery devices loaded with a treatment product(s) for use in aqueous environments e.g. marine and freshwater aquaculture, within the ornamental fish/pet industry or other similar applications. The device acts as a nonedible depot for the medication that facilitates that a controlled or sustained release of the drug is achieved. The active compound/pharmaceutical will be either adsorbed to the outer surface of the device, or alternatively will be impregnated in the polymer matrix of the device. The polymer matrix of the device will be permeable for the active ingredient. Polyvinyl alcohol (PVA) is one example of a polymer that is permeable to lipophilic drugs. Alternatively a biodegradable polymer such as polylactic-co-glycolic acid (PLGA) could be used. Other suitable materials may substitute the materials mentioned in this application.

Using the device of the invention means that through equilibrium partitioning it is possible to maintain a more constant concentration of the therapeutic dose of pesticide over a longer period of time sufficient to ensure that the target organisms are effectively exposed/treated. Furthermore, the amount of chemicals required for treating salmon lice would be significantly reduced.

The invention relates also to a method and system for controlling the level of the drug, hence additional to the slow release device mention above, the invention also comprise a detector/detection process of the level of drug in the fish pen. The detector may be composed of traditional sensors, being arranged in the water masses of the pen. Upon detection of reduced drug levels, a refill operation to increase the drug level may be initiated. The detector may be communicating with an onsite or remote control system and/or surveillance system.

The detector may comprise a plurality of detection means, such as water condition, drug level, lice concentration level (in all stages of life) and more.

Now the invention will be described by some embodiments and the figures.

Figure 1A:
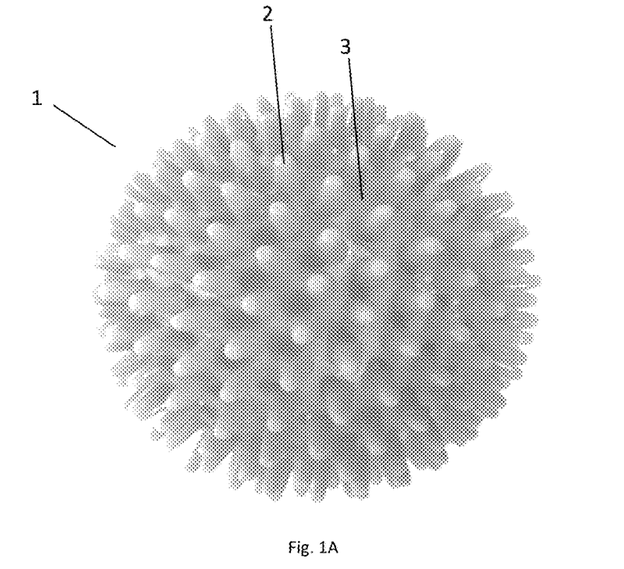
FIG. 1A—Example design of the device of the invention.

In one embodiment of the invention the distribution device 1, as described in FIG. 1A, the distribution device 1 is formed as a ball. The ball may be made of an absorbent and/or permeable material able to contain and dissolve/ release an active agent/drug into a fluid reservoir into which the ball 1 is placed. The distribution device 1 may, float on the surface, in the fluid column or float close to the bottom of the water column (seabed). The ball may be composed of polyurethane, Polyvinyl alcohol, any biodegradable polymers such as polyactic-co-glycolic acid or other. The basic requirement of the material of the distribution device 1 is that it can release the active agent/drug at a controlled rate into the fluid within it is arranged. The distribution device 1 may optionally be made of a material different than a permeable compound, and the active agent may simply be added as an outer layer of the distribution device 1, for example in an impregnation process. The distribution device 1 may be provided with as large a surface as possible to offer the greatest possible distribution rate. In order to increase the outside surface area the distribution device 1, may comprise a plurality of protrusions 2, as shown in the FIG. 1A. Other forms may be devised, both for the distribution device 1 and the protrusions 2. The base 3 of the distribution device may be of same material as the protrusions 2.

Figure 1B:
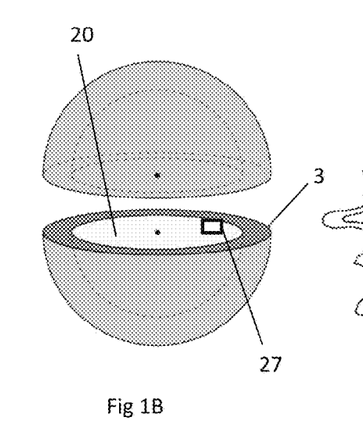

FIG. 1B illustrates a distribution device 1 without the area expanding protrusions on the exterior, further having a hollow structure 20 for containing an active ingredient to be excreted.

Figure 1C:
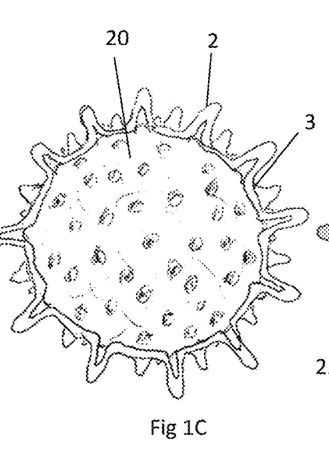

FIG. 1C shows a cross section of a distribution device having an hollow interior 20 and an exterior similar to the distribution device illustrated in FIG. 1A.

Figure 1D:
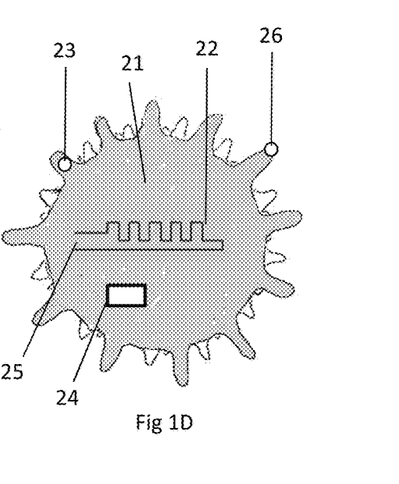

FIG. 1D shows an outline of any of the distribution devices wherein the additional features are illustrated such as heating element 22, battery 25, communication unit 24, and sensors 23, 26.

In one embodiment the distribution device 1 may comprise a controllable internal heating element 22 as illustrated in FIG. 1D, which may control the temperature of the distribution device 1, and by that enabling a better regulation of the distribution rate of the active agent. The device 1 may further comprise: one or more temperature measurement units 23 for measuring outside fluid temperature and/or temperature inside the device 1, a communication unit 24, an energy reserve 25, an outside fluid sampling unit 26, an active ingredient reservoir level 27 and other.

One embodiment of the distribution device may be designed to be used without an active agent and act as a detection device 4, and used solely for measuring the parameters of the fluid volume the distribution device 1 is floating in, such as measuring: active agent concentration in the water, temperature, pH, level of active agent, salinity, and other.

The distribution device 1 may be refilled with active agent in a number of ways. If the distribution device 1 is merely a permeable reservoir, the refilling process may involve filling a hollow structure 20, e.g., an internal reservoir, with the active agent. If the active agent is integrated with the material of the distribution device 1, an alternative for refilling is to bathe the distribution device 1 in a high concentration solution of the active agent for a period of time, the period should be long enough for the distribution device 1 to absorb a desired amount of active agent. In other implementations of the invention it may be necessary to replace the distribution device 1, or simply add more distribution devices 1, when the active agent concentration level in the water falls below required level, instead of refilling depending on type of active agent and material of the distribution device 1.

Figure 2:
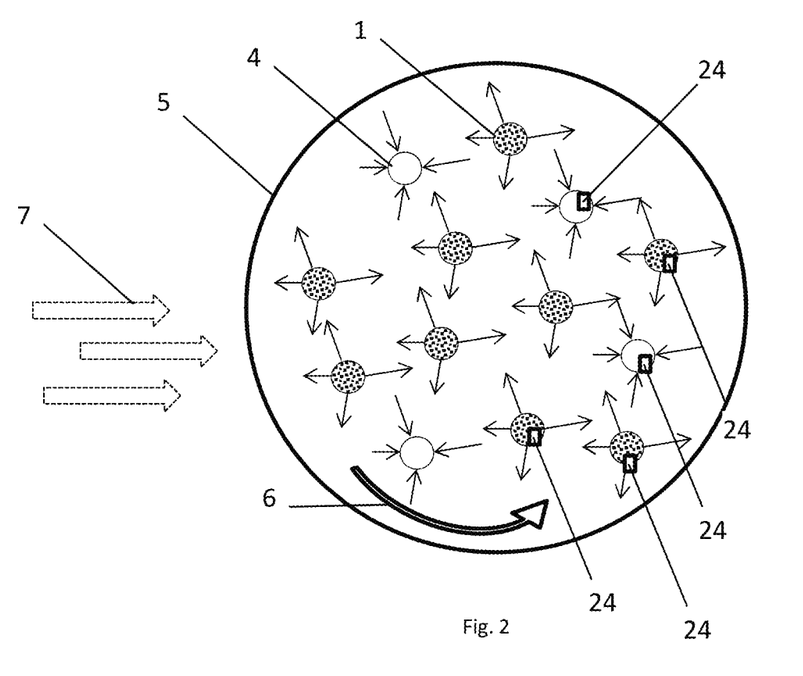

When the environment to be treated with the active agent of the distribution device 1 is a fish pen 5, as described in FIG. 2, the number of distribution device 1 must be adjusted to the requirements to the level of active agent, the speed of the water current 7, the amount of and swimming speed and direction 6 of the fish in the pen 5. In the figure there are two types of devices, one is the distribution device 1, and one is a detection device 4. The detection device may be used to detect parameters such as water temperature, pH, level of active agent, salinity, concentration of pesticide and other, and may similarly to the distribution device 1 comprise a communication unit 24 to enable transmission of detected data to a control system.

Figure 3:
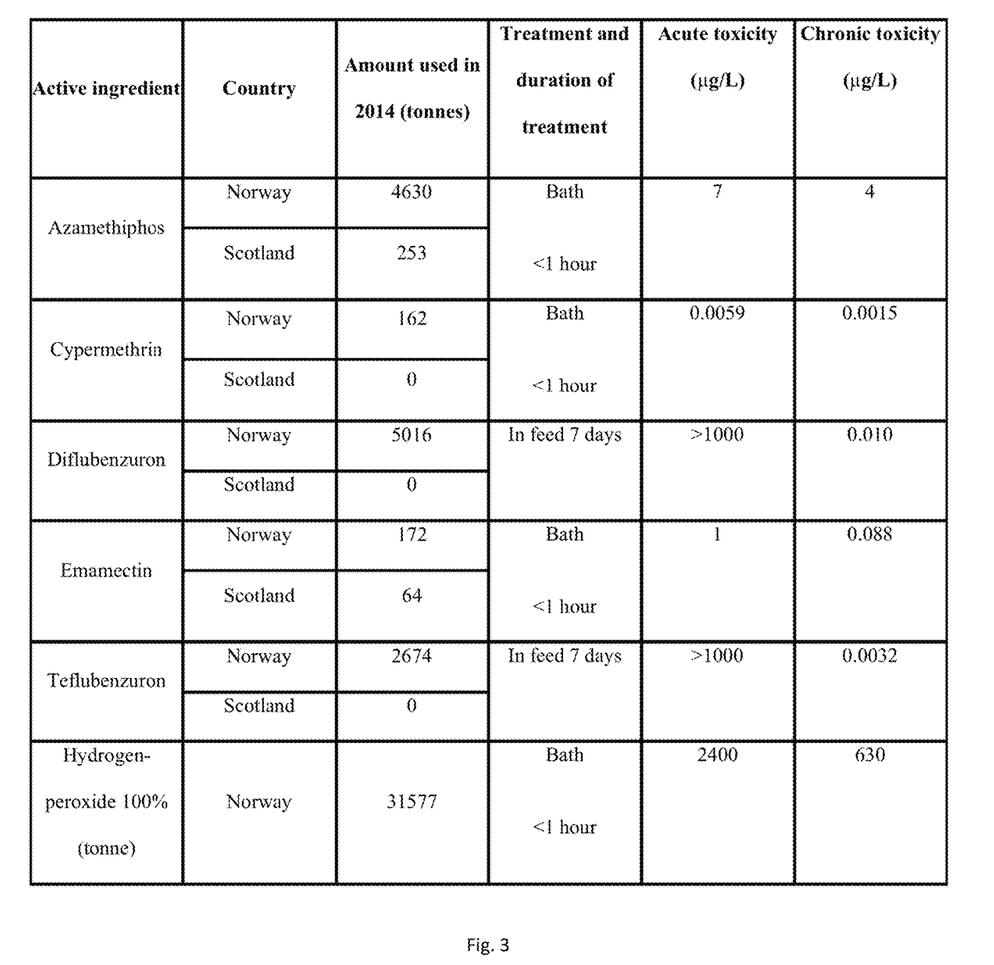

Examples of active agents are described in FIG. 3. This is a non-exhaustive list, but merely an example of ingredients used in Norwegian and Scottish fish industry with amounts of total use (in tons/year) and the typical treatment time for a fish, and what level of the active ingredient is lethal for the treated creatures, such as salmon lice. The present invention will decimate the concentration values of all these active ingredients, far below the toxicity levels defined in the table, when used for achieving the same result, termination of the ectoparasites.

Figure 4:
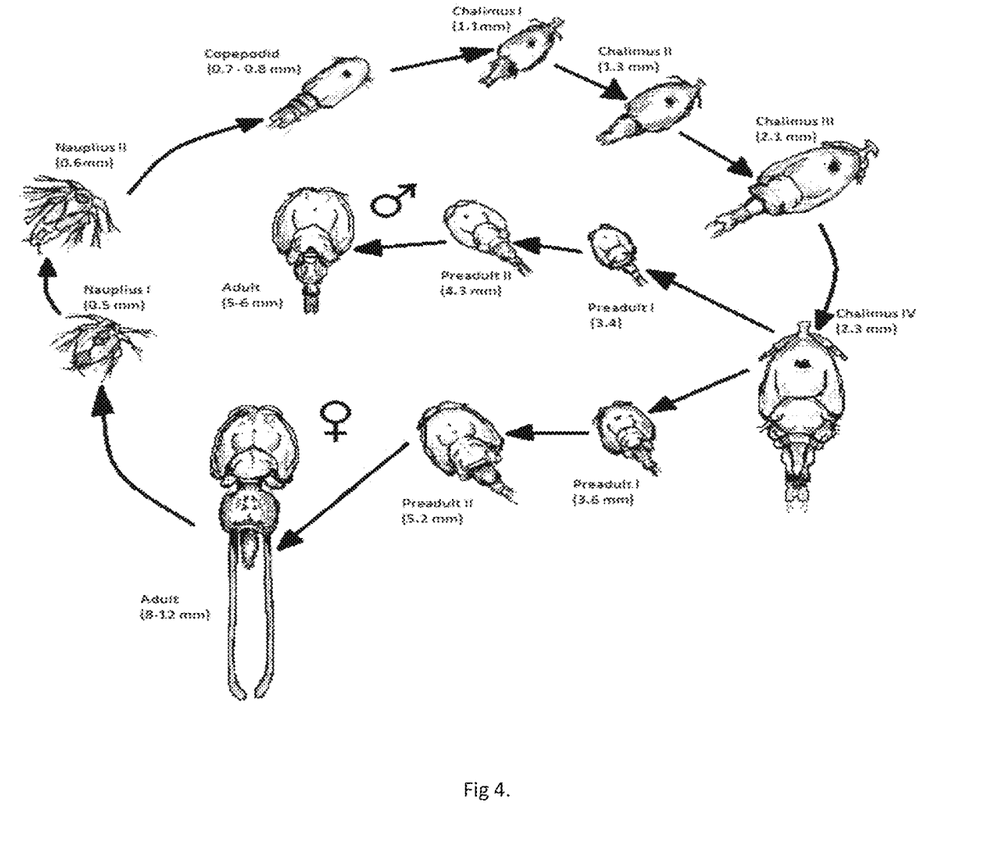

Although the treatment defined in this invention is directed towards the termination of grown ectoparasites infesting the fish in a fish pen, it is easily adaptable to also work preventive on the ectoparasites in earlier stages in their life cycle. In FIG. 4 the life cycle of the salmon lice is outlined. Even if the invention is described implemented in a defined space such as a fish net in a fish pen, as being popular for growing salmon in the sea fjords, there is no limitation to the environment of which the invention can be adapted. It can just as well be used on a location without defined boundaries, such as a net cage, for example as free floating devices in a fjord, a harbor, or other. It is also possible to use the invention in closed environments such as land based fish farms or even domestic aquarium environments.

Figure 5:
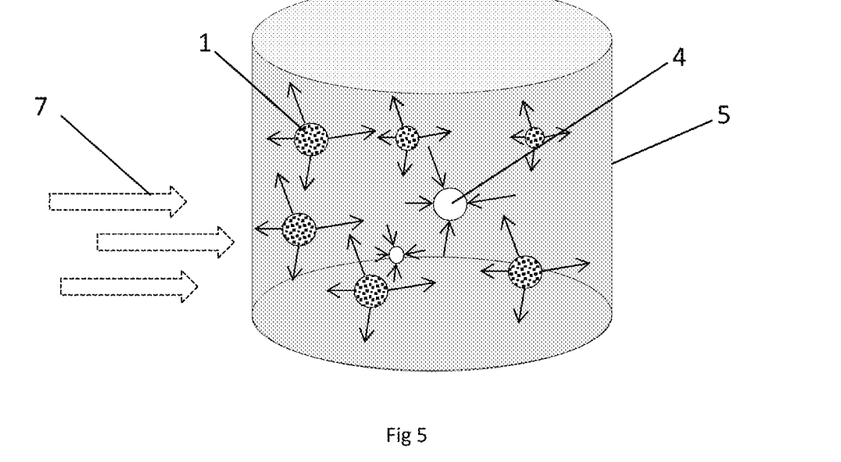

To ensure an even distribution of the active ingredient in the fish pen 5, the arrangement of the distribution devices 1 must be controlled dependent on the flow of water 7, and the swimming pattern 6 of the fish in the pen. If the fish is a bottom fish is will be advisable to ensure that the distribution device 1 is floating or being anchored close to the bottom of the pen. If the flow of water 7 is very low, and the fish has a shoal form of movement pattern with an unpredictable swimming pattern, the distribution device 1 may be free floating.

Figure 6:
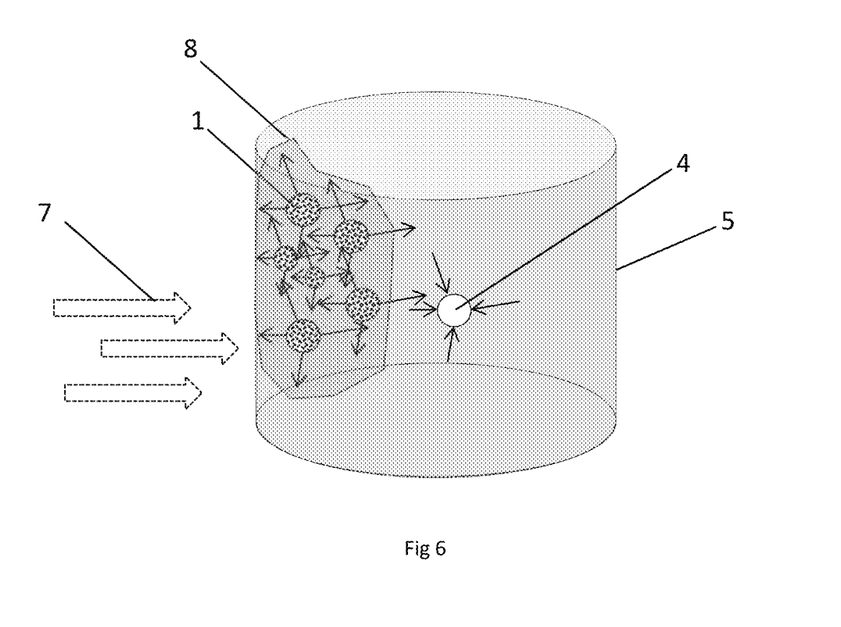

The invention may comprise fastening arrangements such as perforated bags 8 inside the fish pen 5 comprising a number of distribution devices 1, as described in FIG. 6. The bags 8 may be fastened to the pen walls 5 in order to withstand the pressure of the water flow 7. In another arrangement it is provided a rotation device (not shown) moving the distribution device 1 or a bag of a multiple distribution devices 1 in a predefined pattern around inside the fish pen 5. In yet another embodiment the distribution device 1 may be anchored directly to the inside of the fish pen 5 side wall.

Figure 7:
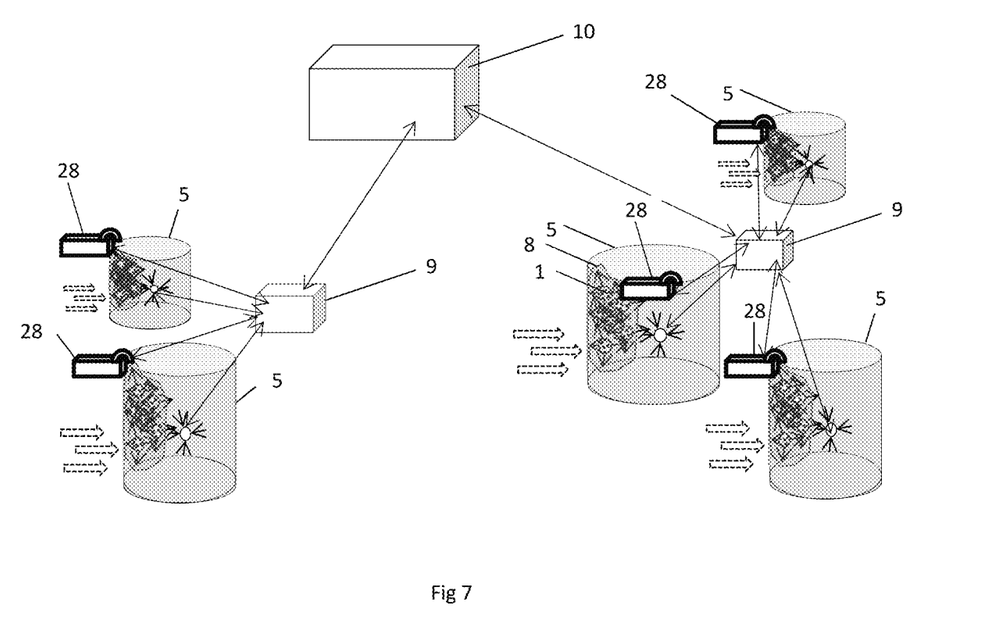

A simplified system overview is described in FIG. 7, where the distribution devices 1 are arranged in the fish pen 5 in a net 8, the detection devices 4 communicates with an adjacent control module 9. The control module communicates with a remote control facility 10. The remote control facility 10 may comprise resources for monitoring, storing, calculation, prediction and displaying values and status related to the task of providing a healthy environment in the fish pen. One control module 9 may communicate with multiple detection devices, located in one or more adjacent fish pens 5. One remote control facility 10 may communicate with a multiple control modules 9.

In one embodiment of the method of the present invention is to introduce a number of distribution devices 1 into a fish pen. Then, over time, the level of pesticide in the water masses inside (and outside) the fish pen is monitored. Every time the pesticide level is outside the recommended level for the long term treatment regime of the system of fish pens, an adjustment to the number of distribution devices in the fish pens is performed. Depending on sea/water currents and quality, it may be necessary to increase or decrease the number of distribution devices 1. The concentration of fish cages in the area will also influence the need for number of distribution devices in the individual fish pen. The method comprises frequent measurement of concentration levels of pesticides. Using a detection device 4 with communication unit 24 may provide this in an autonomous manner. The method may also be a semiautomatic process where the measurement of the pesticide level is manually performed, as well as the replenishment or reduction of distribution devices by providing a replenishment device 28. It may be possible over time to include historical data to enhance controlling the pesticide supply regime, potentially enabling a lower frequency of measurements. Further it is an aim to establish reliable historical data of pesticide concentration, fish health and other parameters to enable an even better optimization of sustained pesticide level.

Figure 8:
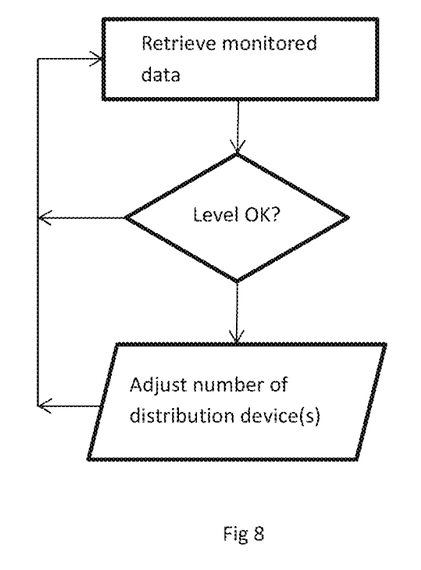

The method may be described in three main operations:
1—test, monitor environment parameters
2—If level is within preset boundaries, repeat step 1
3—If level is outside preset boundaries, adjust number of distribution devices 1

How to perform test and monitor operation is up to the features of the detection device 4, the control module 9, and remote control facility.

Figure 9:
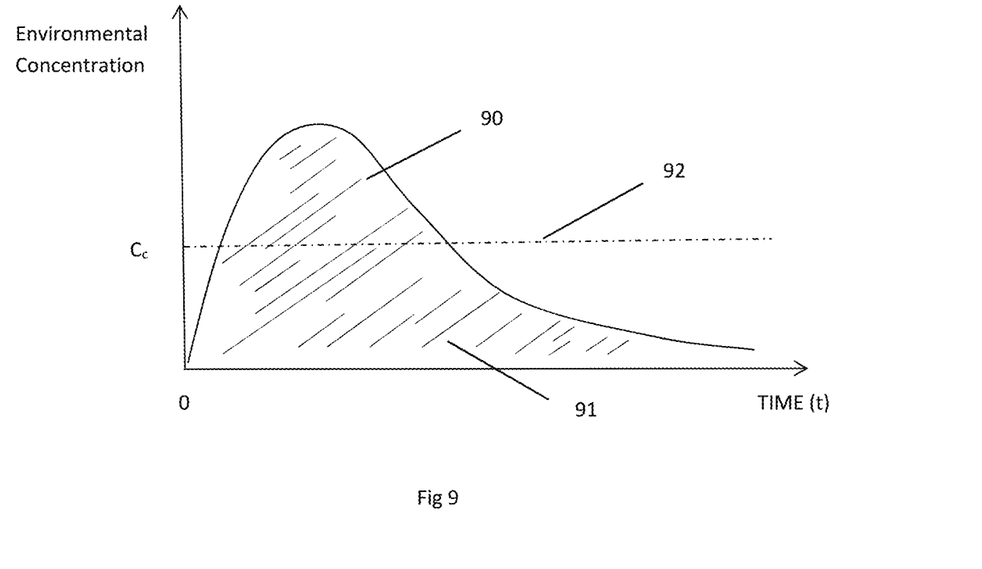

In FIG. 9 it is shown a graph illustrating a therapeutic regime over time according to present state for treating farmed fish in the fish industry. It involves a short pulse dose which is at an environmental concentration above the critical concentration ($C_C$) where adverse effects are likely to occur to non-target organisms. The therapeutic dose capable of for example delousing fish is represented as the area under the curve (AUC) 91, which is the sum of the shaded area (the integral of the curve). The danger zone 90 is shown where the therapeutic dosage is distributed at a rate resulting in an environment concentration above the critical concentration ($C_c$) 92 level.

Figure 10:
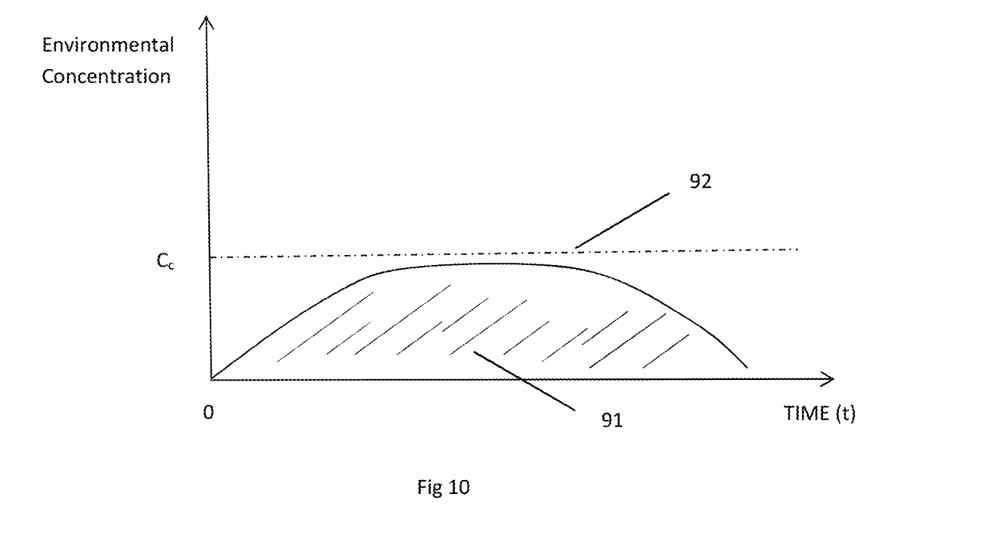

Although the present invention is intended to be used to reduce the total amount of therapeutic dose, it is in FIG. 10 used to show how the invention may facilitate a distribution of therapeutic dose well below the critical concentration ($C_c$) 92 level at all times. In toxicology, the effect of a chemical is defined not only by the concentration but also the duration of exposure. In this figure the total amount of therapeutic dose is the same as in the case of FIG. 9. The difference is that the environmental concentration never rises above the ($C_c$) 92 level, the danger zone.

Figure 11:
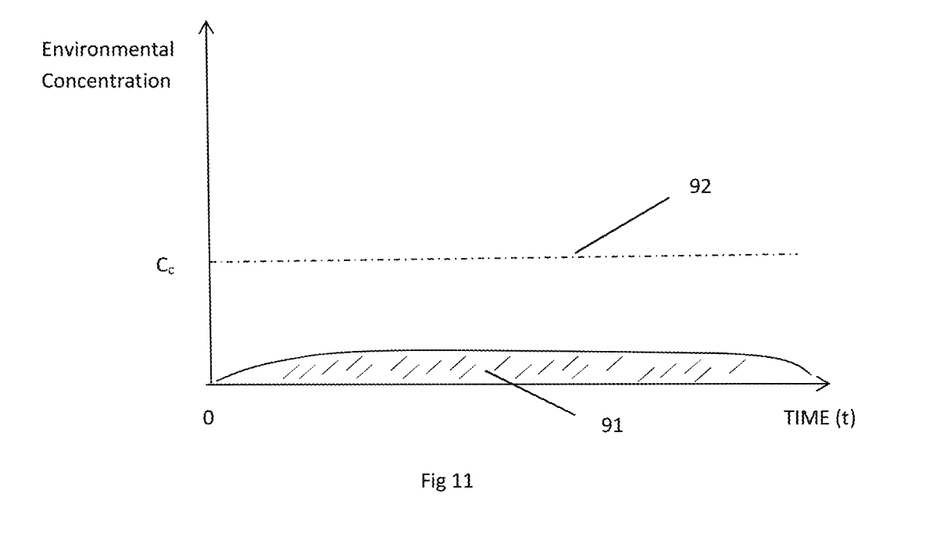

A third regime is shown in FIG. 11, representing a desired future state of implementation of the present invention. Here the exposure duration is further extended by a sustained continuous release resulting in the same AUC but which is significantly below the ($C_c$) 92. The result is a lot less harmful for the environment, and may even prove to reduce the overall use of active agents, but not reducing the effect of desired control of target organisms.

The invention may comprise an automatic replacement unit 28 able to add or retrieve distribution devices to/from the fish pen when level is outside preset boundaries, that is if the level is below desired level, the system adds more distribution devices 1 to the fish pen 5, and if the level is above the desired level, the system retrieves one or more or all of the distribution devices 1. Alternatively the test results may be evaluated and provide a required change in number of distribution devices 1 or level of distribution of pesticides. The actual adjustment of pesticide may be manually administered by a person onsite.

The invention can also be described as a first device embodiment of a distribution device for treatment of fluid comprising a body comprising a base (3) for carrying the pesticide, a pesticide, the pesticide being comprised in the distribution device, wherein the pesticide being able to be excreted into a volume of fluid when the body (3) is brought in contact with the fluid.

A second device embodiment of device for treatment of fluid according to the first device embodiment, further comprising one or more protrusions (2) for increasing the area of the device and thereby the contact area between the pesticide carrier and the fluid in which it is released.

A third device embodiment of device for treatment of fluid according to one of the first or second device embodiment, wherein the device is made of a porous material able to hold and release, at a controlled rate, the pesticide.

A fourth device embodiment of device for treatment of fluid according to one of the first or second device embodiment, wherein the device is covered by a surface substance able to hold and release, at a controlled rate, the pesticide.

A fifth device embodiment of device for treatment of fluid according to one of the first or second device embodiment, wherein the device comprise a hollow structure, and is further made of a porous material allowing a content of the hollow structure to be exerted through the base and protrusions to the environment outside the device.

A sixth device embodiment of device for treatment of fluid according to the fifth device embodiment, wherein the pesticide is contained within the hollow structure.

A seventh device embodiment of device for treatment of fluid according to any of the first to sixth device embodiment, wherein the device being made of a material being one of, or a combination of: Polyurethane, Polyvinyl alcohol, any biodegradable polymers such as polylactic-co-glycolic acid or other.

An eight device embodiment of device for treatment of fluid according to any of the second to seventh device embodiment, further comprising a sensor arrangement for determining the level of pesticide concentration in the fluid outside the device 4.

A seventh device embodiment of device for treatment of fluid according to any of the first to eight device embodiment, wherein the device further comprise a communication unit for communicating with a remote controller.

A tenth device embodiment of device for treatment of fluid according to any of the first to ninth device embodiment, wherein the device further comprise a heating device, for warming up the device or part of the device, in order to increase pesticide exertion rate.

An eleventh device embodiment of device for treatment of fluid according to one of the ninth or tenth device embodiment, wherein the communication unit controls one or both of sensor arrangement and heating device.

An twelfth device embodiment of device for treatment of fluid according to any of the second to eleventh device embodiment, further comprising a sensor arrangement for determining characteristics of the fluid outside the device (4), such as one or more of: temperature, pH, level of active agent, salinity, and other.

The invention can also be described as a first method embodiment for distributing pesticide in a fish pen, the method comprising the step of defining a critical concentration level of pesticide inside the fish pen; defining the fraction of critical concentration level of pesticide inside the fish pen is required for long term treatment of the fish in the fish pen necessary to terminate infestations and sickness in fish population inside fish pen; measuring a level of pesticide in the fish pen; when measured level of pesticide is below required pesticide level for long term medication adding a number of distribution devices according to any of the first to twelfth device embodiments described above inside the fish pen, and when measured level of pesticide is above a predefined fraction of a critical concentration level in the fish pen retrieve a number of distribution devices according to any of the first to twelfth device embodiments described above inside the fish pen.

A second method embodiment according to the first method embodiment, wherein the measurement of the pesticide level in the fish pen, and addition or subtraction of distribution devices are automated.

A third method embodiment according to any of the first to second method embodiment, wherein the addition or subtraction of distribution devices are decided based on historical measured data for the fish pen.

The invention can also be described as a first system embodiment for controlling pesticide release in a fish pen, the system comprising: one or a plurality of fish pen, one or a plurality of distribution devices according to any of the first to twelfth device embodiments described above, and a fluid monitoring device for determining the pesticide level of the water in the fish pen.

A second system embodiment according to the first system embodiment, further comprising a remote control center, and a communication unit for communicating monitoring data to and from the monitoring device to the remote control center.

A third system embodiment according to the first or second system embodiment, further comprising a replenish device for adjustment of the number of distribution devices in each fish pen.

A fourth system embodiment according to the third system embodiment, further comprising a control signal originating from either the monitoring device or the communication unit for controlling the replenish devises.

A fifth system embodiment according to any of the first to fourth system embodiment, wherein there is a plurality of communication units, each communication units communicating with a preset number of fish pens, and all the communication units communicate with the same remote control center.

The invention claimed is:

1. A distribution device for treating a fluid, comprising:

a pesticide, a body comprising a base for carrying the pesticide, wherein the pesticide is able to be excreted into a volume of fluid when the body is brought in contact with the fluid, one or more protrusions for increasing an area of the device and thereby a contact area between the base for carrying the pesticide and the fluid in which it is released, and a sensor arrangement configured to determine a level of pesticide concentration in the fluid outside the device.

2. The device according to claim 1, wherein the body is made of a porous material able to hold and release, at a controlled rate, the pesticide.

3. The device according to claim 1, wherein a surface of the device is able to hold and release, at a controlled rate, the pesticide.

4. The device according to claim 1, wherein the body comprises a hollow structure, and is further made of a porous material allowing a content of the hollow structure to be exerted through the base and the one or more protrusions to an environment outside the device.

5. The device according to claim 4, wherein the pesticide is contained within the hollow structure.

6. The device according to claim 1, wherein the body is made of a material comprising one or more of a Polyurethane, a Polyvinyl alcohol, or any biodegradable polymer.

7. The device according to claim 1, further comprising a control module configured to communicate with a remote controller.

8. The device according to claim 1, further comprising a heating device configured to warm up the device or part of the device, in order to increase pesticide exertion rate.

9. The device according to claim 7, wherein the control module is configured to control one or both of the sensor arrangement or a heating device.

10. The device according to claim 1, wherein the sensor arrangement is further configured to determine one or more characteristics of the fluid outside the device, wherein the one or more characteristics comprise one or more of: temperature, pH, level of active agent, or salinity.

11. A method for distributing pesticide in a fish pen, comprising:

defining a first critical concentration level of pesticide inside the fish pen;

defining a second critical concentration level of pesticide inside the fish pen, wherein the second critical concentration level is a level for long term treatment of the fish in the fish pen sufficient to terminate infestations and sickness in fish population inside fish pen;

measuring a level of pesticide in the fish pen;

in response to the measured level of pesticide being below the second critical concentration level for long term treatment, adding a first number of distribution devices according to claim 1 inside the fish pen, and in response to the measured level of pesticide being at or above the second critical concentration level, retrieving a second number of the distribution devices from inside the fish pen.

12. The method according to claim 11, wherein the measuring of the pesticide level in the fish pen, and the adding or the retrieving of distribution devices are automated.

13. The method according to claim 11, wherein the adding or retrieving of distribution devices are determined based on historically measured data for the fish pen.

14. A system for controlling pesticide release in a fish pen, comprising:

at least one fish pen having water, at least one distribution devices according to claim 1, and a fluid monitoring device including the sensor arrangement for determining a pesticide level of the water in the fish pen.

15. The system according to claim 14, further comprising a remote control center, and a communication unit configured to communicate monitoring data to and from the fluid monitoring device to the remote control center.

16. The system according to claim 14, further comprising at least one replenishing device configured to adjust a number of the distribution devices in each fish pen.

17. The system according to claim 16, further comprising a control signal originating from either the fluid monitoring device or the communication unit, wherein the control signal controls the at least one replenishing device.

18. The system according to claim 14, further comprising a plurality of control modules, each control module configured to communicate with a preset number of fish pens, and all the control modules configured to communicate with a same remote control center.

* * * * *